United States Patent [19]

Cook, Jr. et al.

[11] 4,320,070

[45] Mar. 16, 1982

[54] PROCESS FOR PREPARING CHLOROTHIOLFORMATES

[75] Inventors: James A. Cook, Jr.; William A. Keim, both of Barberton, Ohio

[73] Assignee: PPG Industries, Inc., Pittsburgh, Pa.

[21] Appl. No.: 213,511

[22] Filed: Dec. 8, 1980

Related U.S. Application Data

[63] Continuation-in-part of Ser. No. 78,329, Sep. 24, 1979, abandoned.

[51] Int. Cl.³ .................. C07C 155/02; C07C 154/00
[52] U.S. Cl. .............................. 260/455 A; 260/455 B
[58] Field of Search ........................ 260/455 B, 455 A

[56] References Cited

U.S. PATENT DOCUMENTS

| | | | |
|---|---|---|---|
| 2,913,327 | 11/1959 | Tilles et al. | 260/455 R |
| 3,093,537 | 6/1963 | Tilles | 260/455 R |
| 3,126,406 | 3/1964 | Tilles et al. | 260/455 A |
| 3,165,544 | 1/1965 | Tilles et al. | 260/455 R |
| 3,175,897 | 3/1965 | Tilles et al. | 260/455 A |
| 3,185,720 | 5/1965 | Tilles et al. | 260/455 A |
| 3,299,114 | 1/1967 | Tilles et al. | 260/455 R |
| 4,012,405 | 3/1977 | Alesandrini | 260/455 R |
| 4,119,659 | 10/1978 | Alesandrini | 260/455 R |

OTHER PUBLICATIONS

Calmon and Kressman, Ion Exchangers in Organic and Biochemistry, Interscience Pub. Ind., New York, 1957 (p. 659).

*Primary Examiner*—Henry R. Jiles
*Assistant Examiner*—Robert C. Whittenbaugh
*Attorney, Agent, or Firm*—Irwin M. Stein

[57] ABSTRACT

Chlorothiolformates are prepared by reacting a mercaptan with phosgene in the presence of a catalytic amount of anion exchange resin in the neutral salt form. Preferably the resin has quaternary ammonium functionality.

23 Claims, No Drawings

PROCESS FOR PREPARING CHLOROTHIOLFORMATES

CROSS REFERENCE TO RELATED APPLICATIONS

This application is a continuation-in-part of our co-pending U.S. Patent Application, Ser. No. 078,329, filed Sept. 24, 1979, entitled PROCESS FOR PREPARING CHLOROTHIOLFORMATES, now abandoned.

DESCRIPTION OF THE INVENTION

The catalytic preparation of alkyl and phenyl chlorothiolformates by reaction of the appropriate mercaptan, e.g., an alkyl or phenyl mercaptan, with phosgene has been described in the patent literature. In the absence of catalyst, the reaction can require several days to achieve substantially complete reaction. Exemplary of U.S. Patents directed to the preparation of chlorothiolformates are U.S. Pat. Nos. 3,165,544, 3,093,537, 4,012,405 and 4,119,659, which describe the use of activated carbon for the preparation of alkyl and phenyl chlorothiolformates, and U.S. Pat. No. 3,299,114, which describes the use of tertiary amines and heterocyclic amine compounds to catalyze the aforesaid reaction.

It has now been discovered that anion exchange resins in the neutral salt form can be used to catalyze the reaction of mercaptan with phosgene. More particularly, the neutral salt form of ion exchange resins having quaternary ammonium functionality (strongly basic anion exchange resins) or polyamine functionality (weakly basic anion exchange resins) on a polymeric backbone can be used as the catalyst.

DETAILED DESCRIPTION OF THE INVENTION

Certain chlorothiolformates, e.g. ethyl chlorothiolformate, have been found useful as pesticides. See, for example, U.S. Pat. No. 3,093,537. In addition, chlorothiolformates, e.g., ethyl chlorothiolformate, have been found useful as intermediates for the preparation of herbicidally effective thiolcarbamates and similar compounds. See, for example, U.S. Pat. Nos. 2,913,327, 3,126,406, 3,175,897 and 3,185,720. In the latter two patents, chlorothiolformate is reacted further with an amine to produce the corresponding thiolcarbamate.

The present invention relates to the use of anion exchange resin in the neutral salt form as a catalyst for the reaction of mercaptan with phosgene to produce chlorothiolformates. More particularly, the neutral salt form of anion exchange resin, which has been pretreated to be substantially waterfree, is used. The reaction can be represented by the following balanced equation:

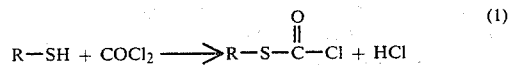

$$R-SH + COCl_2 \longrightarrow R-S-\overset{O}{\overset{\|}{C}}-Cl + HCl \quad (1)$$

According to the present invention, in the reaction of mercaptan with phosgene depicted by equation (1), the catalytically active species of anion exchange resin is the neutral salt form. Therefore, in practicing this invention, one can either directly utilize the neutral salt form of the anion exchange resin, or alternatively, one can utilize the basic form of the resin since the hydrochloric acid generated by the reaction of mercaptan with phosgene acts to convert the basic form to the neutral salt form during the course of the reaction. The result is identical in both alternatives; that is, the neutral salt form is the active species.

The anion exchange resins which are used as catalysts in the foresaid reaction are well-known materials, and many are commercially available. They are, as a matter of trade usage, referred to as "basic", for the reason that in many applications the resin is converted to the basic form prior to use. Generally, anion exchange resins are sold in the neutral salt form because this form is chemically more stable than any converted form. Both conversion to the basic form and regeneration subsequent to use are typically performed by washing with a base such as, for example, sodium hydroxide.

Anionic exchange resins contain primary, secondary and tertiary amine groups, and quaternary ammonium groups on a three dimensional polymeric hydrocarbon backbone. The resins are typically categorized into two groups, i.e., the strongly basic anion exchange resin (quaternary ammonium groups) and weakly basic anion exchange groups (polyamine functional groups). The neutral salt form of either group can be used as the catalyst in the practice of the present process. These ion exchange resins consist of two principal parts-a structural portion (polymer matrix) and a functional portion. The wide variety of ion-exchange resin formulations and properties derives from various combinations of these parts.

The polymer matrix is typically formed from polymers (including copolymers) produced by condensation or addition polymerization. Condensation polymers useful as ion-exchange resin backbones are high molecular weight, cross-linked structures formed usually by an ionic organic reaction mechanism from small polyfunctional monomers such as by the condensation of phenol with formaldehyde or an epoxide, e.g., epichlorohydrin, with an amine or ammonia. Addition polymers useful as the backbone for ion-exchange resins are cross-linked structures formed by the free-radical polymerization of mixtures of olefinic and diolefinic compounds, e.g., by the polymerization of styrene and divinyl benzene. The addition polymers are generally more stable to hydrolysis or oxidative cleavage and therefore are preferred.

Commercially available anion exchange resins are typically of the styrene-divinyl benzene backbone type. The amount of divinyl benzene copolymerized with styrene commonly varies from about 1 to 16, e.g., 4 to 12, more usually about 8, percent of divinyl benzene. The copolymer product is usually prepared by the free-radical suspension polymerization of the monomers. The polymer is then modified by chlorination or chloromethylation using chloromethyl methylether and a Friedel-Crafts condensation catalyst. The resulting modified polymer is reacted with an amine, polyamine or ammonia to form the ion-exchange resin. For example, the chlorinated polymer can be reacted with a tertiary amine in the presence of a polar solvent such as water to form a quaternary ammonium salt. Amination of the chlorinated polymer can be conducted with alkyl amines or alkaline polyamines to produce a variety of strong and weak basic anion exchange resins.

The resins which contain quaternary ammonium functionality are considered to be strong basic anion exchange resins; while the resins which possess an amine or polyamine functionality are considered to be weak basic anion exchange resins. Although the neutral ionic form exhibited by the resin can vary, the ionic form most common for ion exchange resins is the chloride form, i.e., the anion associated with the amine functional group.

As commerically prepared for sale, anion exchange resins also typically contain about 20 percent to 50 percent water. The reaction of mercaptan with phosgene depicted in equation (1) is more preferably conducted under anhydrous conditions since, in the presence of water, the chlorothiolformate product decomposes into HCl and $CO_2$. Consequently, it is preferred the neutral salt form of the anion exchange resin used as catalyst is substantially free of water, i.e., less than 0.1 percent $H_2O$. Thus, the resin is easily dried by treating with methanol to displace water and then heating in a vacuum oven to remove residual methanol. Slight traces of methanol, i.e., less than 0.1 percent, may remain and this will be converted to methyl chloroformate and dimethyl carbonate by reaction with phosgene during the process. Drying to anhydrous form can be performed on the anion exchange resin either as it is commercially obtained in granular form or, if desired, the resin may be dried after it is packed into a column. Either alternative yields equivalent results.

The anion exchange resins utilized in the present process will typically be in bead form and vary in size from about 400 mesh to about 16 mesh. Although gel-type resins can be utilized, the granular or spherical (bead) form are preferred for use as a catalyst in the present process. Also available are the macroporous or macroreticular resins which have pores of considerably larger size then the more conventional gel-type resins. The physical form of the catalyst chosen should be such that the resin resists physical degradation by the forces it encounters in the reaction, e.g., by attrition. Further, the resin should be somewhat chemically resistant to the chemical species encountered by the resin, i.e., the reactants and the reaction products of the mercaptan-phosgene reaction.

Use of a solid granular anion exchange resin as a catalyst in the present process has the advantage that the resin is substantially insoluble in the reaction medium and, because it is a solid, it can be separated easily by filtration or decantation when the reaction is completed. The solid resin can be put in a column and the present process operated continuously by charging mercaptan and phosgene continuously to the column. Alternatively, the solid resin can be charged to a continuously stirred reaction vessel and the reaction performed on a batch or semi-continuous basis. The resin catalyst should also provide a reduction in catalyst costs over the conventional amine catalysts for the reason that they can be used repeatedly and usually without regeneration.

Among the anion exchange resins that can be used in the present process, there can be mentioned those resins sold under the trademarks DUOLITE ®, DOWEX ®, IONAC ®, AMBERLITE ® and AMBERLYST ®. Exemplary of the latter two commercial resins are in the AMBERLITE IRA-900 series ion exchange resins, the AMBERLITE IRA-93 ion exchange resins, and the macroreticular AMBERLYST A-26 and A-29 ion exchange resins.

The amount of anion exchange resin used to catalyze the reaction of the mercaptan with phosgene is that amount which is required to accelerate the reaction to commercially acceptable rates, i.e., a catalytic amount. Whereas several days may be required to accomplish significant conversions of mercaptan, e.g., greater than 80 percent conversion, in the absence of catalyst, such conversions can be accomplished within 0.1 to 5 hours with use of anion exchange resin in the salt form as catalyst. Typically, between about 5 and about 40 grams, e.g., 20 grams, of resin per 100 grams of mercaptan will be used when the reaction is conducted in a stirred reactor. When the process is performed continuously, as in a column, the amount of resin used is less precise for the reason that the same catalyst is used for the continuously charged reactants and until the catalyst becomes deactivated. Stated differently, sufficient resin is used to provide between about 0.001 and 0.2 moles of ion exchange capacity per mole of mercaptan charged. More typically the resin will provide between about 0.01 and 0.1, e.g., 0.05 moles of ion exchange capacity per mole of mercaptan charged.

In the case of a batch or semi-continuous process, the anion exchange resin is typically added to the reactor separately from the phosgene or mercaptan. In a preferred embodiment, a pool of phosgene, i.e., the excess phosgene, is established in the reactor and the resin catalyst added to the phosgene before the introduction of the mercaptan and additional phosgene reactants. The reactants can be introduced into a suitable reactor in any order or simultaneously: however, it is preferable to add the mercaptan to a pool of phosgene. Thus, all of the reactants can be added simultaneously with stirring to the reactor (as in a batch process) and permitted to react. In the case of a batch process, it is preferable to add the mercaptan slowly to the phosgene so as to control the heat of reaction and minimize the formation of by-product dithiolcarbonate. When phosgene is added to a pool of mercaptan, the reaction commences at a higher temperature than when the order of reactant introduction is reversed. These higher temperatures and the stoichiometry favor the formation of by-product dithiolcarbonate.

More preferably, the phosgene and mercaptan are charged simultaneously and slowly to a pool of excess phosgene with stirring, e.g., over a period of 6–10 hours, followed by post stirring for about one hour. This latter method (semi-continuous) avoids the presence in the reactor of large amounts of unreacted material and permits the gradual build-up of product in the reactor. The post stirring period allows time for substantially complete reaction of the mercaptan and can be performed in a series of reactors, e.g., holding tanks, other than the principal reactor.

In the case of a continuous process, the resin is charged to a reactor, e.g., a column, and the mercaptan and phosgene charged to the reactor simultaneously. After a suitable residence time, the product is removed from the reactor. The continuous process can be operated as a plug flow system (as in the case of a column reactor) or a series of sequential reactors in which the effluent of a reactor is forwarded to the next reactor in the series. Sufficient residence time in the reactor(s) is provided to insure substantially complete reaction of the mercaptan reactant.

In a further embodiment, it is contemplated that the reaction be conducted by introducing the reactants into a heel of the reaction medium, i.e., chlorothiolformate. Although the initial reaction temperature is higher than when mercaptan is added to a pool of phosgene, reaction times are shorter.

Mercaptans that can be reacted with phosgene in the presence of the anion exchange resin catalyst can be represented by the formula, R—SH, wherein R is alkyl, cycloalkyl, cycloalkylmethyl, lower alkenyl, aryl, alkaryl, aralkyl, haloaryl, haloalkyl, and carboalkoxy alkyl. Such mercaptans are well recognized in the art, as can be seen by reference to the aforesaid recited U.S. patents. Mercaptans, such as those described herein, can be prepared by methods known in the art. Among the methods described in the art for preparing mercaptans are the reaction of an alkali alkyl sulfate or alkyl halide with sodium or potassium hydrosulfide: the vapor phase reaction of the appropriate alcohol with hydrogen sulfide: and the addition of hydrogen sulfide to the appropriate unsaturated organic compound.

Typically, R in the formula R—SH is a branched or straight chain $C_1$–$C_{15}$ alkyl, $C_2$–$C_5$ alkenyl, $C_3$–$C_7$ cycloalkyl or cycloalkylmethyl, $C_6$–$C_{10}$ aryl, $C_6$–$C_{10}$ alkaryl or aralkyl, $C_6$–$C_{10}$ haloaryl or haloalkyl or $C_2$–$C_{10}$ carboalkoxyalkyl radical. The halo prefix in the aforesaid radicals includes the halogen substituents, i.e., chloro, bromo, fluoro and iodo, preferably chloro and bromo. Generally the aliphatic and aromatic radicals described with respect to the secondary amine are also suitable as substituents for the R group of the mercaptan. More typically, R is a $C_1$–$C_{10}$, preferably $C_1$–$C_6$ alkyl, $C_3$–$C_4$ alkenyl, $C_5$–$C_6$ cycloalkyl or cycloalkylmethyl, phenyl, $C_1$–$C_4$ alkyl substituted phenyl, chlorophenyl, including mono- and polychlorinated phenyl, benzyl and chlorobenzyl, including mono- and polychlorinated benzyl, or $C_2$–$C_5$ carboalkoxyalkyl radical.

Examples of organic mercaptans which can be suitably used in the reaction of the present invention are alkyl mercaptans such as methylmercaptan, ethylmercaptan, isopropylmercaptan, n-propylmercaptan, isobutylmercaptan, secondary butylmercaptan, n-butylmercaptan, 2-pentylmercaptan, neopentylmercaptan, n-pentylmercaptan, n-hexylmercaptan, neohexylmercaptan, n-heptylmercaptan, n-octylmercaptan, and the like. As examples of cycloalkyl mercaptans, the following can be mentioned: cyclopentylmercaptan, cyclohexylmercaptan, 2-methylcyclohexylmercaptan, 3-methylcyclohexylmercaptan, cyclopropylmethylmercaptan, cyclopentylmethylmercaptan, cyclohexylmethylmercaptan, and the like. Allyl mercaptan and butenyl mercaptan are typical examples of lower alkenyl mercaptans that can be used in the above defined reaction.

Also useful are aryl, alkaryl, aralkyl, haloaryl and haloalkyl compounds exemplified by the following compounds: mercaptobenzene, 2-mercaptonaphthalene, 4-mercaptotoluene, 2-mercaptotoluene, 3-mercaptotoluene, 2,4-dimethylmercaptobenzene, 2,5-dimethylmercaptobenzene, 4-tert-butylmercaptobenzene, 1-methyl-2-mercaptonaphthalene, 4-ethylmercaptobenzene, benzylmercaptan, mercaptoethyl benzene, mercaptopropyl benzene, triphenylmethyl mercaptan, mercaptomethyl naphthalene, mercaptoethyl naphthalene, mercaptobutyl naphthalene, 2-chloromercaptobenzene, 3-chloromercaptobenzene, 4-chloromercaptobenzene, 2,5-dichloromercaptobenzene, 4-bromomercaptobenzene, 2-iodomercaptobenzene, 3-iodomercaptobenzene, 4-iodomercaptobenzene, 2-chlorobenzylmercaptan, 3-chlorobenzylmercaptan, 4-chlorobenzylmercaptan, 2,4-dichlorobenzylmercaptan, 3,4-dichlorobenzylmercaptan, 4-bromobenzylmercaptan, 4-chloro-1-mercaptonaphthalene, 4-bromo-1-mercaptonaphthalene, and the like. Similarly, examples of carboalkoxyalkyl mercaptans that can be reacted with phosgene according to the present invention are those compounds typified as esters of mercapto-acids. Suitable examples are methyl mercaptoacetate, ethyl mercaptoacetate, propyl mercaptoacetate, butyl mercaptoacetate, pentyl mercaptoacetate, hexyl mercaptoacetate, methyl 2-mercaptopropionate, ethyl 2-mercaptopropionate, pentyl 2-mercaptopropionate, methyl 3-mercaptopropionate, ethyl 3-mercaptopropionate, hexyl 3-mercaptopropionate, methyl 2-mercaptobutyrate, propyl 2-mercaptobutyrate, hexyl 2-mercaptobutyrate, methyl 3-mercaptobutyrate, ethyl 3-mercaptobutyrate, hexyl 3-mercaptobutyrate, methyl 4-mercaptobutyrate, ethyl 4-mercaptobutyrate, hexyl 4-mercaptobutyrate, methyl 3-mercaptovalerate, ethyl 3-mercaptovalerate, hexyl 3-mercaptovalerate, methyl 5-mercaptovalerate, ethyl 5-mercaptovalerate, hexyl 5-mercaptovalerate, and the like.

The amount of phosgene used in the reaction can vary; but is typically at least a stoichiometric amount based on equation (1). That is, at least one mole of phosgene is used for every mole of mercaptan. More usually, an excess of phosgene, e.g., from about 5 to about 50 mole percent excess phosgene, based on the mercaptan is used for the reasons that the phosgene can be removed more readily from the reaction mixture and an excess of mercaptan favors the production of by-product dithiolcarbonate.

Reaction of the mercaptan with phosgene is commonly conducted at atmospheric pressure, although subatmospheric or superatmospheric pressures can be used. Reaction temperatures should be maintained as low as possible, consonant with reasonable reaction rates since, at high temperatures, by-product dithiolcarbonate can be formed in significant amounts. Since the mercaptans and chlorothiolformates described hereinbefore exhibit varying reactivities and varying decomposition temperatures such factors must be taken into account in selecting the reaction temperature. Commonly, reaction temperatures will be less than about 70° C. With an excess of phosgene, the reaction temperature will typically range between about 0° C. and about 70° C. at atmospheric pressure and with refluxing phosgene. More typically, reaction temperatures will range between about 10° C. and about 50° C., e.g., between 10° C. and 35° C.

The chlorothiolformate product prepared in accordance with the present process contains low levels of organic disulfide, i.e., R—S—S—R, and dithiolcarbonate by-products. The low level of disulfide impurity is in contrast to the significant quantities of such impurity that is found in chlorothiolformates prepared using activated carbon as the catalyst. See, for example, U.S. Pat. No. 4,012,405 (column 1) wherein from 3 to 7 percent of diethyl disulfide is produced during preparation of ethyl chlorothiolformate by reaction of ethyl mercaptan with phosgene in the presence of activated carbon catalyst. Further, the anion exchange resin catalyst of the present process does not appear to catalyze the reaction of the chlorothiolformate with further mercaptan to produce the dithiolcarbonate by-product.

In conducting the reaction of the present process, the reaction mixture is usually agitated to assist in removing heat from the reactor. At the end of a batch or semi-continuous reaction, excess phosgene is removed from the products mixture, e.g., by stripping. Phosgene can be stripped from the chlorothiolformate product by pulling a vacuum on the system—thereby permitting the phosgene to boil off: passing an inert gas, e.g., nitrogen, through the reaction mixture: or, heating the reaction mixture slightly to boil off the excess phosgene. The resin catalyst can be separated from the reaction product by decantation or filtration.

The degassed chlorothiolformate product is obtained in sufficient purity to be used in most commercial applications, e.g., as an intermediate for the preparation of thiolcarbamates. If further purification is desired, the chlorothiolformates can be distilled or recrystallized from a suitable solvent to obtain a more pure product.

If the chlorothiolformate is to be converted to a thiolcarbamate, secondary amine is reacted with the chlorothiolformate product in the presence of an acid acceptor, e.g., sodium hydroxide. The amount of amine used is that amount required to convert all of the chlorothiolformate to the corresponding thiolcarbamate.

In a typical embodiment of a batch process, about 0.6 mole of phosgene per mole of mercaptan used is condensed in a reactor to establish a pool of phosgene at about 10° C. AMBERLYST A-26 anion exchange resin containing a total of 0.05 mole of ion exchange capacity per mole of mercaptan used is added to the phosgene and ethyl mercaptan is introduced slowly into the reactor simultaneously with the further addition of about 0.6 mole of phosgene per mole of mercaptan used. The additional phosgene and mercaptan reactant are added to the reactor over a period of about one hour and the reaction maintained under constant agitation. Vaporized phosgene is condensed in a reflux condenser connected to the reactor and condensed phosgene returned to the reactor. As the reaction takes place, the phosgene and ethyl mercaptan are consumed and the boiling point of the reaction mixture rises from about 10° C. to about 27° C. at the end of the reaction. At the end of about 2 to 3 hours, excess phosgene and unreacted ethyl mercaptan are stripped from the reactor by degassing and the chlorothiolformate product removed from the reactor.

While the above embodiment has been exemplified by ethyl mercaptan and AMBERLYST anion exchange resin, other of the described mercaptans or anion exchange resins can be substituted for the ethyl mercaptan, and AMBERLYST resin respectively of the exemplification and expect to obtain the corresponding chlorothiolformate.

The present invention is more particularly described in the following example which is intended as illustrative only since numerous modifications and variations therein will be apparent to those skilled in the art. In the examples, the purity of the chlorothiolformate product is reported as peak area percent, i.e., by estimating the area under the peaks of the chart produced by gas liquid chromatographic analysis.

EXAMPLE I

Phosgene (1.8 moles) was condensed into a one liter, round bottom, three-neck flask containing 17.74 grams of AMBERLYST A-26 anion exchange resin in the neutral chloride salt form having 0.075 moles of ion exchange capacity. The resin had been washed with methanol to remove moisture contained in the commercial product and the methanol removed by heating the washed resin in a nitrogen stream. The flask was equipped with a stirrer and motor, thermometer, addition funnel, phosgene inlet tube and a dry ice-acetone condenser and cooled with a wet ice bath. 1.5 moles of ethyl mercaptan was placed in the addition funnel and added to the reaction flask over a period of 20 minutes with stirring. The temperature of the phosgene in the reaction flask at the start of ethyl mercaptan addition was about 7° C. The ice bath was not used during the addition of the ethyl mercaptan. The temperature of the reaction mixture at the end of the addition of ethyl mercaptan was about 9° C.

The reaction mixture was stirred for about 2-½ hours. The reaction was followed by means of gas liquid chromatographic analysis (GLC) of the unreacted ethyl mercaptan. The temperature of the reaction mixture was controlled at about 20° C. by means of the ice bath. The crude reaction product was identified by GLC as ethyl chlorothiolformate of about 90 percent purity. It was estimated that the ethyl chlorothiolformate product contained about 9.5 percent phosgene, 0.25 percent ethyl mercaptan, and trace amounts of diethyl disulfide (DEDS) and diethyl dithiolcarbonate (DETC). A very small amount of methyl chloroformate and dimethylcarbonate was found by GLC and mass spectrometer analysis of the chlorothiolformate product. These materials are believed to have been formed from traces of methanol not removed from the washed resin.

EXAMPLE II

Using the same resin and reaction mixture that was used in Example I, a further 1.5 moles of ethyl mercaptan and 1.8 moles of phosgene were added to the reaction mixture over a period of 13 minutes and the mixture maintained at about 20° C. The crude undegassed reaction mixture was stirred for about 3-½ hours. The reaction mixture was found to contain about 91 percent ethyl chlorothiolformate, 7.8 percent phosgene, 1.1 percent ethyl mercaptan and traces of diethyl disulfide and diethyl dithiolcarbonate.

EXAMPLE III

With the same resin and reaction mixture of Example II still in the reaction flask, the reaction mixture was heated to about 40° C. and phosgene (0.76 mole) added to the flask until phosgene refluxing occurred. Ethyl mercaptan (0.63 mole) was then added to the flask in about 4 minutes and the reaction mixture stirred for about 1-½ hours. The reaction mixture was maintained at about 35° C. for 90 minutes to yield a crude product which, when analyzed, was found to contain 90 percent ethyl chlorothiolformate, 9 percent phosgene, 0.2 percent ethyl mercaptan, 0.1 percent diethyl dithiolcarbonate and a trace of diethyl disulfide.

The data of Examples I, II and III show that anion exchange resin in the neutral salt form catalyzes the reaction of mercaptan with phosgene to produce chlorothiolformate with little by-product formation. The catalyst of Example I was used also in the runs described in Examples II and III and was still catalytically active for those latter two experimental runs.

Although the present process has been described with reference to specific details of certain embodiments thereof, it is not intended that such details should be regarded as limitations upon the scope of the invention except as and to the extent that they are included in the accompanying claims.

We claim:

1. In the process of preparing organic chlorothiolformates by reacting an organic mercaptan having the formula,

R—SH with phosgene, wherein R is alkyl, cycloalkyl, cycloalkylmethyl, lower alkenyl, aryl, alkaryl, aralkyl, haloaryl, haloaralkyl, and carboalkoxy alkyl, the improvement which comprises conducting said reaction in the presence of a catalytic amount of anion exchange resin, the functional groups of said resin being selected from the group consisting of polyamine and quaternary ammonium functional groups, said resin being present in the neutral salt form.

2. The process of claim 1 wherein the ion exchange resin has quaternary ammonium functionality.

3. The process of claim 2 wherein the resin is in the form of a chloride salt.

4. The process of claim 1 wherein the ion exchange resin has polymaine functionality.

5. The process of claims 1, 2 or 3 wherein the anion exchange resin is substantially water-free.

6. The process of claims 1, 2, or 4 wherein the backbone of the resin is a styrene-divinylbenzene copolymer.

7. The process of claims 1, 2, 3 or 4 wherein the amount of basic anion exchange resin used contains between 0.001 and about 0.2 moles of ion exchange capacity per mole of mercaptan used.

8. The process of claim 7 wherein from about 5 to about 50 mole percent excess phosgene is used.

9. The process of claim 7 wherein the reaction is conducted by adding the mercaptan to a pool of phosgene.

10. The process of claim 1 wherein R of the formula R—SH is a branched or straight chain $C_1$-$C_{15}$ alkyl, $C_2$-$C_5$ alkenyl, $C_3$-$C_7$ cycloalkyl or cycloalkylmethyl, $C_6$-$C_{10}$ aryl, $C_6$-$C_{10}$ alkaryl or aralkyl, $C_6$-$C_{10}$ haloaryl or haloaralkyl or $C_2$-$C_{10}$ carboalkoxyalkyl radial.

11. The process of claim 1 wherein R of the formula R—SH is a branched or straight chain $C_1$-$C_{10}$ alkyl radical.

12. In the process of preparing alkylthiolformates by reacting an alkyl mercaptan having the formula R—SH, wherein R is a $C_1$-$C_6$ alkyl, with phosgene, the improvement which comprises conducting said reaction in the presence of a catalytic amount of an anion exchange resin having quaternary ammonium functionality, said resin being in the form of a neutral salt.

13. The process of claim 12 wherein the resin has a styrene-divinyl-benzene copolymer backbone.

14. The process of claim 13 wherein the amount of resin used contains between about 0.001 and about 0.2 moles of ion exchange capacity per mole of mercaptan used.

15. The process of claim 14 wherein from about 5 to about 50 mole percent excess phosgene is used.

16. The process of claim 15 wherein the reaction is conducted by adding the mercaptan to a pool of phosgene.

17. A process which comprises reacting an organic mercaptan having the formula, R—SH, wherein R is a $C_1$-$C_6$ alkyl, with phosgene, said phosgene being present in amounts of from about 5 to 50 mole percent excess, in the presence of a catalytic amount of anion exchange resin, the functional groups of said resin being selected from the group consisting of polyamine and quaternary ammonium functional groups, said resin being present in the neutral salt form, to thereby produce a reaction product comprising the corresponding alkyl chlorothiolformate, removing excess phosgene from the reaction product, and mixing secondary amine of the formula $R_1R_2NH$, wherein $R_1$ and $R_2$ are each selected from the group consisting of $C_1$-$C_4$ alkyl, cyclohexyl and allyl, to the phosgene depleted reaction product in amounts sufficent to convert the alkyl chlorothiolformate to the corresponding alkyl thiolcarbamate.

18. The process of claim 17 wherein the resin has quaternary ammonium functionality.

19. The process of claim 18 wherein the backbone of the resin is a styrene-divinylbenzene copolymer.

20. The process of claim 19 wherein the resin is present as a chloride salt.

21. The process of claims 17, 18 or 20 wherein the resin used provides from 0.001 to about 0.2 moles of ion exchange capacity per mole of mercaptan used.

22. The process of claim 21 wherein R is ethyl or propyl and $R_1$ and $R_2$ are each selected from group consisting of $C_2$-$C_4$ alkyl, cyclohexyl and allyl.

23. The process of claim 22 wherein the secondary amine is selected from the group consisting of diethylamine, di-n-propylamine, di-n-butylamine, di-isobutylamine, ethyl cyclohexylamine, or di-allylamine.

* * * * *